United States Patent
Weferling et al.

(12)

(10) Patent No.: US 6,232,493 B1
(45) Date of Patent: *May 15, 2001

(54) PROCESS FOR PREPARING METAL SALTS OF ARYLALKYLPHOSPHINIC ACIDS

(75) Inventors: Norbert Weferling, Hürth; Hans-Peter Schmitz, Brühl, both of (DE)

(73) Assignee: Clariant GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/198,539

(22) Filed: Nov. 24, 1998

(30) Foreign Application Priority Data

Nov. 28, 1997 (DE) .............................. 197 52 727
Nov. 10, 1998 (DE) .............................. 198 51 774

(51) Int. Cl.$^7$ ..................................... C07F 9/30
(52) U.S. Cl. ................................................ 562/8
(58) Field of Search ........................ 562/8; 524/133

(56) References Cited

U.S. PATENT DOCUMENTS

| 3,912,654 | 10/1975 | Heid et al. ........................... 252/321 |
| 3,914,345 | 10/1975 | Kleiner et al. ....................... 260/970 |
| 4,185,031 | * 1/1980 | Gillman et al. ...................... 562/25 |
| 4,208,322 | 6/1980 | Sandler ......................... 260/45.75 K |
| 4,321,187 | 3/1982 | Granzow .............................. 524/133 |
| 4,590,014 | * 5/1986 | Wolf . |
| 4,594,199 | * 6/1986 | Thottahil . |
| 4,632,741 | 12/1986 | Wolf et al. ....................... 204/157.73 |
| 4,939,285 | 7/1990 | Weis et al. ........................... 558/214 |
| 4,972,011 | 11/1990 | Richardson et al. ................. 524/130 |
| 4,973,727 | 11/1990 | Gainer et al. ........................ 558/133 |

FOREIGN PATENT DOCUMENTS

| 0327496 | 8/1989 | (EP) . |
| 8505520 | 5/1984 | (ES) . |

OTHER PUBLICATIONS

Chem abs vol 64 abstract No. 16661g by Hoffmann, Jun. 1966.*

CA:107:17690 abs of Bull Chem Soc Jpn by Ohno 60(8) pp 2945–51, 1987.*

CA:107:25119 abs of ES532346, Jun. 1985.*

E.E. Nifant'ev: "Acid catalysis in the hydrophosphorylation of olefins" Journal of General Chemistry USSR., vol. 50, No. 8/1,—Aug. 1980, pp. 1416–1423, XP002093427, New York US.

E.E. Nifant'ev: "Hydrophosphorylation of cyclopentenes" Journal of General Chemistry USSR., vol. 61, No. 1/1,—Jan. 1991, pp. 83–92, XP002093428 New York US.

Chemical Abstracts, vol. 69, No. 16, Oct. 14, 1968 Columbus, OH, US; abstract No. 067487, p. 6310; column 2; XP002093429 & Petrov K.A.: "Dialkylphosphinic acids" Khim. Org. Soedin. Fosfora. Akad. Nauk SSSR, OTD. Obshch. Tekh. Khim., 1967, pp. 181–186, SU.

Synthesis of DI(n–octyl)phosphinic acid. Influence of the sulfuric acide in the phosphination of 1–octene with sodium hypophosphite, M. Martinez, C. Herranz, N. Miralles, & A. Sastre, Afinidad LIII, 466, 1996, pp. 404–406.

Houben–Weyl, Methoden der organischen Chemie, vol. XII/1, 4$^{th}$ Edition, 1963, pp 228ff.

"Phosphinsaure und deren Derivate," Dr. Felcht, vol. E2, 1982, pp. 123 ff.

CA:120:245501 abs of JPO5194562, Aug. 1993.*

* cited by examiner

*Primary Examiner*—Jean F. Vollano
(74) *Attorney, Agent, or Firm*—Susan S. Jackson; Scott E. Hanf

(57) ABSTRACT

The invention relates to a process for preparing metal salts of arylalkylphosphinic acids, which comprises:

a) reacting olefins with arylphosphonous acids or alkali metal salts thereof in the presence of a cationic free-radical initiator, and b) reacting the arylalkylphosphinic acids or alkali metal salts thereof obtained by a) with metal compounds of Mg, Ca, Al, Sb, Sn, Ge, Ti, Zn, Fe, Zr, Ce, Bi, Sr, Mn, Li, Na and/or K to give the metal arylalkylphosphinate salts.

The invention also relates to the use of the products prepared by the abovementioned process for preparing flame retardants.

9 Claims, No Drawings

PROCESS FOR PREPARING METAL SALTS OF ARYLALKYLPHOSPHINIC ACIDS

The invention relates to a process for preparing metal salts of arylalkylphosphinic acids and to the use of the compounds prepared by this process.

Aluminum salts of dialkylphosphinic acids are known as flame retardants (EP 0 699 708 A1). They can be prepared by various processes.

DE 24 47 727 A1 describes low-flammability polyamide molding compounds which comprise a salt of a phosphinic acid or of a diphosphinic acid.

EP-A-0 699 708 describes flame-retardant polyester molding compounds, the polyesters being given a flame-retardant finish by adding calcium salts or aluminum salts of phosphinic acid or diphosphinic acid. The abovementioned salts are obtained by reacting the corresponding dialkylphosphinic acids with calcium hydroxide or aluminum hydroxide.

The abovementioned processes have the disadvantage, in particular, that they start from starting compounds which cannot be prepared industrially, or can only be prepared with great expenditure.

However, no process which can be carried out industrially is known to date by which metal salts of arylalkylphosphinic acids can be prepared.

The object underlying the invention is to provide a process for preparing metal salts of arylalkylphosphinic acids which leads to the desired end products in a simple manner.

This object is achieved by a process of the type described at the outset, which comprises a) reacting olefins with arylphosphonous acids and/or alkali metal salts thereof in the presence of a cationic free-radical initiator, and b) reacting the arylalkylphosphinic acids and/or alkali metal salts thereof obtained by a) with metal compounds of Mg, Ca, Al, Sb, Sn, Ge, Ti, Zn, Fe, Zr, Ce, Bi, Sr, Mn, Li, Na and/or K to give the metal arylalkylphosphinate salts.

Preferably, the olefins are unbranched or branched α-olefins.

Preferably, the olefins are ethylene, n-propylene, isopropylene, n-butene, isobutene, n-pentene, isopentene, n-hexene, isohexene, n-octene, isooctene, 1-decene, 1-dodecene, 1-tetradecene, 1-hexadecene, n-eicosene and/or 2,4,4-trimethylpentene isomer mixture.

Preferably, as olefins, use is made of those having an internal double bond, cyclic or open-chain dienes and/or polyenes having from 4 to 20 carbon atoms.

Preferably, the olefins bear a functional group.

Suitable olefins are compounds of the formula

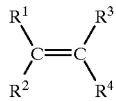

where $R^1$–$R^4$ can be identical or different and are hydrogen, an alkyl group having from 1 to 18 carbon atoms, phenyl, benzyl or alkyl-substituted aromatics.

Suitable compounds are likewise cycloolefins of the formula

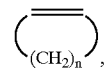

in particular cyclopentene, cyclohexene, cyclooctene and cyclodecene.

Use can also be made of open-chain dienes of the formula

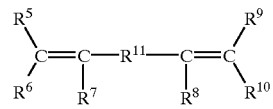

where $R^5$–$R^{10}$ are identical or different and are hydrogen or a $C_1$ to $C_6$ alkyl group and $R^{11}$ is $(CH_2)_n$ where n=0 to 6. Preference is given in this case to butadiene, isoprene and 1,5-hexadiene.

Preferred cyclodienes are 1,3-cyclopentadiene, dicyclopentadiene and 1,5-cyclooctadiene and norbornadiene.

Preferably, the arylphosphonous acid and/or alkali metal salts thereof are phenylphosphonous acid and/or alkali metal salts thereof.

Preferably, the aryl radical of the arylalkylphosphinic acids and arylphosphonous acids is an aromatic having from 6 to 12 carbon atoms, which can be monosubstituted or polysubstituted by halogens, hydroxyl, aryl, alkyl, ether, ester, keto, carboxyl, sulfonyl and/or chloroalkyl groups.

Preferably, the azo compounds are cationic and/or non-cationic azo compounds.

Preferably, as cationic azo compounds, use is made of 2,2'-azobis(2-amidinopropane) dihydrochloride or 2,2'-azobis(N,N'-dimethyleneisobutyramidine) dihydrochloride.

Compounds which are also suitable according to the invention are non-cationic azo compounds such as azobis(isobutyronitrile), 4,4'-azobis(4-cyanopentanoic acid) and 2,2'-azobis(2-methylbutyronitrile).

Compounds which are likewise suitable according to the invention as free-radical initiators are inorganic peroxide free-radical initiators (hydrogen peroxide, ammonium peroxodisulfate, potassium peroxodisulfate etc.) and/or organic peroxide free-radical initiators (dibenzoyl peroxide, di-tert-butyl peroxide, peracetic acid, etc.).

A broad selection of suitable free-radical initiators may be found, for example, in Houben-Weyl, Supplementary Volume 20 in the chapter "Polymerisation durch radikalische Initiierung" [Polymerization by free-radical initiation] on pages 15–74.

Preferably, the metal compounds are metal oxides, metal hydroxides, metal hydroxideoxides, metal sulfates, metal acetates, metal nitrates, metal chlorides and/or metal alkoxides.

Particularly preferably, the metal compounds are aluminum hydroxide or aluminum sulfates.

Preferably, the reaction is carried out in the presence of carboxylic acids.

Particularly preferably, the carboxylic acid is acetic acid.

Preferably, the reaction is carried out at a temperature of from 40 to 130° C.

Particularly preferably, the reaction is carried out at a temperature of from 60 to 100° C.

In particular, the process is preferably carried out at a temperature of from 80 to 95° C.

Preferably, the reaction is carried out in a pressure reactor. This applies in particular if the boiling point of the olefins is below the reaction temperature.

The reaction in step b) here is carried out after adjusting to a pH range for the salt precipitation which is optimum for the respective arylalkylphosphinic acid/metal compound system.

The invention also relates to the use of the arylalkylphosphinic acids and/or alkali metal salts thereof obtained by the process described above for preparing flame retardants.

The invention likewise relates to the use of the arylalkylphosphinic acids and/or alkali metal salts thereof obtained by the process described above for preparing flame retardants for thermoplastic polymers such as poly(ethylene terephthalate), poly(butylene terephthalate), polystyrene or polyamide, and for thermosetting plastics.

The arylalkylphosphinic acids and/or metal salts thereof obtained by the process described above are also used as additives in polymeric compounds, as extraction media and surfactants.

The invention is described by the examples below.

EXAMPLE 1 a) Preparation of the arylalkylphosphinic acid 500 g (3.5 mol) of phenylphosphonous acid were charged, together with 4 kg of acetic acid, into a 16 l pressure reactor. Then, the mixture was heated with stirring to an internal temperature of 85° C. and ethylene was forced in until saturation was reached at 5 bar. 27 g (100 mmol, equivalent to 3 mol %, based on the phenylphosphonous acid used) of 2,2'-azobis(2-amidinopropane) dihydrochloride, dissolved in 100 ml of water, were thereafter added in the course of 3 hours. The exothermic reaction was controlled by the metering rate of the abovementioned free-radical initiator solution in such a manner that a maximum reaction temperature of 95° C. was reached. During the further reaction, ethylene was resupplied, so that the pressure over the entire period of the experiment was maintained at about 5 bar. The mixture was then allowed to continue to react for a further 3 h at 85° C. The reactor was then depressurized and cooled. The mass of the contents was 4.7 kg (100% of theory).

| $^{31}$P-NMR analysis: | phenylphosphonous acid: | 1.3 mol % |
|---|---|---|
| | phenylethylphosphinic acid: | 85.2 mol % |
| | phenylbutylphosphinic acid: | 10.0 mol % |
| | unknown components: | 3.5 mol % | b) Preparation of the aluminum salts of phenylethylphosphinic and phenylbutylphosphinic acid A solution of 165 g (0.25 mol) of aluminum sulfate hydrate in 300 ml of water was added to 1 kg of the solution produced by step a) and the mixture was heated to 45° C. with stirring.

25% strength sodium hydroxide solution was then added until the pH was between 4.5 and 4.9. Precipitation of the aluminum phosphinates was then completed by heating the suspension at 85° C. for two hours.

After cooling at room temperature, the suspension was filtered via a vacuum filter and the residue was washed with water and acetone. After drying the product in a vacuum drying cabinet at 120° C., 116 g of a colorless powder were obtained. The yield was 91% of theory.

Analytical Values phosphorus: found 16.9%, calculated 17.2% (w/w)

aluminum: found 5.2%, calculated 5.0% (w/w)

What is claimed is:

1. A process for preparing metal salts of phenylalkylphosphinic acids having no halogen substituents, which comprises a) reacting olefins having no halogen substituents with phenylphosphonous acids, alkali metal salts of the phenylphosphonous acids or a combination thereof in the presence of a free-radical initiator having an azo-group, and b) reacting the phenylalkylphosphinic acids, the alkali metal salts of the phenylalkylphosphinic acids or a combination thereof obtained by a) with metal compounds of Mg, Ca, Al, Sb, Sn, Ge, Ti, Zn, Fe, Zr, Ce, Bi, Sr, Mn, Li, Na and/or K to give the metal phenylalkylphosphinate salts.

2. The process as claimed in claim 1, wherein the halogen-free olefins are ethylene, n-propylene, isopropylene, n-butene, isobutene, n-pentene, isopentene, n-hexene, or isohexene.

3. The process as claimed in claim 1, wherein the initiator is 2,2'-azobis(2-amidinopropane) dihydrochloride, 2,2'-azobis(2-methylbutyronitrile) or 2,2'-azobis(N,N'-dimethyleneisobutyramidine) dihydrochloride.

4. The process as claimed in claim 1, wherein the reaction is carried out in the presence of carboxylic acids.

5. The process as claimed in claim 4, wherein the carboxylic acid is acetic acid.

6. The process as claimed in claim 1, wherein the reaction is carried out at a temperature of from 40 to 130° C.

7. The process as claimed in claim 1, wherein the reaction is carried out at a temperature of from 80 to 130° C.

8. The process as claimed in claim 1, wherein the metal compounds are metal oxides, metal hydroxides, metal hydroxideoxides, metal sulfates, metal acetates, metal nitrates, metal chlorides and/or metal alkoxides.

9. The process as claimed in claim 1, wherein the reaction is carried out in a pressure reactor.

* * * * *